United States Patent [19]

Sultan et al.

[11] Patent Number: 5,515,714
[45] Date of Patent: May 14, 1996

[54] VAPOR COMPOSITION AND FLOW SENSOR

[75] Inventors: Michel F. Sultan; Charles R. Harrington, both of Troy; Michael J. O'Rourke, Warren, all of Mich.

[73] Assignee: General Motors Corporation, Detroit, Mich.

[21] Appl. No.: 341,258

[22] Filed: Nov. 17, 1994

[51] Int. Cl.$^6$ .................... G01N 25/00; G01F 1/684
[52] U.S. Cl. .................. 73/25.01; 73/204.26; 73/204.18
[58] Field of Search ................ 73/25.01, 25.05, 73/204.18, 204.25, 204.26

[56] References Cited

U.S. PATENT DOCUMENTS

| | | | |
|---|---|---|---|
| 4,332,157 | 6/1982 | Zemel et al. | 73/204.23 |
| 4,501,144 | 2/1985 | Higashi et al. | 73/204.26 |
| 4,576,050 | 3/1986 | Lambert | 73/861.05 |
| 4,651,564 | 3/1987 | Johnson et al. | 73/204.26 |
| 4,713,970 | 12/1987 | Lambert | 73/861.05 |
| 4,782,708 | 11/1988 | Harrington et al. | 73/861.05 |
| 4,993,261 | 2/1991 | Lambert | 73/204.21 |
| 5,024,083 | 6/1991 | Inada et al. | 73/204.26 |
| 5,086,650 | 2/1992 | Harrington et al. | 73/204.26 |
| 5,089,783 | 2/1992 | Kapsokavathis et al. | 324/672 |
| 5,103,184 | 4/1992 | Kapsokavathis et al. | 324/672 |
| 5,260,665 | 11/1993 | Goldberg et al. | 324/636 |
| 5,263,380 | 11/1993 | Sultan et al. | 73/204.26 |
| 5,335,555 | 8/1994 | Guizot et al. | 73/861.95 |

*Primary Examiner*—Hezron E. Williams
*Assistant Examiner*—Daniel S. Larkin
*Attorney, Agent, or Firm*—Timothy G. Gorbatoff

[57] ABSTRACT

The present invention is directed to a single solid state thermal diffusion sensor capable of measuring both the composition and flow of gaseous vapors traveling through a duct. The sensor comprises two orthogonal sensing patterns, each having a heating element positioned equidistant between two thermistor elements. The heaters and thermistors are made from thin film platinum deposited on a thermally insulating polyimide layer having low thermal diffusivity. A sinusoidal voltage is applied to each heating element for generating oscillating thermal waves which propagate through the gaseous vapor to their respective thermistors. The thermistors of a first, transversely positioned sensing pattern are responsive to both the composition and flow of the gaseous vapor, while the thermistors of a second, longitudinally positioned sensing pattern are responsive only to the composition of the gaseous vapor. Appropriate electronic circuitry utilizes the responses of the thermistor pairs for determining the composition and flow of the gaseous vapor.

6 Claims, 9 Drawing Sheets

| FIG. 9B | FIG. 9C |
|---------|---------|
| FIG. 9A |         |

VAPOR COMPOSITION AND FLOW SENSOR

This invention relates to vapor sensors, and more particularly, to a solid state thermal diffusion sensor capable of measuring both the composition and flow of a gaseous vapor.

BACKGROUND OF THE INVENTION

Various types of sensors have been proposed for detecting the composition or flow of a gaseous vapor traveling through a duct. Very few, if any, can detect both composition and flow simultaneously and unambiguously. Sensors responsive to composition or flow have be based upon tin oxide, optical, hot wire and acoustical technologies.

Tin oxide sensors are nonlinear and quite sensitive at very low concentration levels only. Optical sensors include infrared absorption techniques. They have shown some promise in this area, but the technology has not yet been fully developed. Hot wire sensors respond simultaneously to gas composition and flow, without giving independent information on any of the two quantities. Acoustic type sensors may be designed to respond to gas composition alone, or to both gas composition and flow. To date, the spectral stability of their piezoelectric transducers over a wide temperature operating range is somewhat suspect.

As an alternative to using a single sensor to measure both composition and flow, multiple sensors can be utilized, each sensing a different parameter. For example, one sensing composition and another sensing flow. However, the use of multiple sensing technologies for measuring composition and flow independently has the inherent disadvantages of increasing the developmental, packaging and installation costs of the sensing system. Therefore, there is a desire to develop a single sensor which can measure both the composition and flow of gaseous vapors traveling through a duct. Typical applications would include automotive vehicle air/fuel monitoring and control, as well as gas tank canister purge control for meeting future vehicle emission requirements.

SUMMARY OF THE INVENTION

The present invention is directed to a single solid state thermal diffusion sensor capable of measuring both the composition and flow of gaseous vapors traveling through a duct. The invention operates on the principle that the propagation of heat waves in a gas flow duct varies with respect to the composition and flow of gas through the duct.

Structurally, the sensor of the present invention comprises an integrated circuit chip with two orthogonal sensing patterns, each consisting of a heating element positioned between two detecting thermistor elements. The heaters and thermistors are made from thin film platinum deposited on a thermally insulating polyimide layer having low thermal diffusivity. One of the sensing patterns responds to both the composition and flow of the gaseous vapor, while the other sensing pattern responds only to the composition of the gaseous vapor. Appropriate circuitry determines the gaseous vapor composition and flow based upon the responses of the two sensing patterns.

According to one aspect of the present invention, a first heating element is positioned transversely with respect to the flow of the gaseous vapor, and located equidistant between two thermistor elements, one upstream and one downstream. A sinusoidal voltage is applied to the first heating element for generating oscillating thermal waves which propagate through the gaseous vapor to its respective adjacent thermistors. Both the magnitude and phase of the thermal oscillations detected upstream and downstream of the heater by the thermistors change rapidly with changes in the composition and flow of the gaseous vapor. The difference between the responses of the upstream and downstream thermistors provides for an output voltage signal corresponding to the composition and flow of the gaseous vapor.

According to another aspect of the present invention, a second heating element is positioned longitudinally with respect to the flow of the gaseous vapor, and similarly located equidistant between two thermistor elements. As with the transversal sensor, a sinusoidal voltage is applied to the second heating element for generating varying thermal waves which propagate through the gaseous vapor to its respective adjacent thermistors. The effect of vapor flow upon the propagation of the oscillating thermal waves is negligible because of the longitudinal orientation of the second heating element and thermistors. Both the magnitude and phase of the thermal oscillations detected by the longitudinal thermistors change rapidly with changes in the composition of the gaseous vapor. A sum of the responses of the longitudinal thermistors provides for an output voltage signal corresponding to the composition of the gaseous vapor.

Coupled with appropriate electronic circuitry, the output voltage signals provided by the two orthogonal sensing patterns are responsive to the composition and flow of the gaseous vapor, and enable an accurate determination of both the composition and flow of the gaseous vapors flowing within the duct. This is achieved with only one sensor which is positioned in the center of the duct through which the gaseous vapor is flowing. Requiring only a single sensor, rather than two separate sensors, minimizes developmental, packaging and installation costs.

These and other aspects and advantages of the invention may be best understood by reference to the following detailed description of the preferred embodiments, when considered in conjunction with the accompanying drawings.

DETAILED DESCRIPTION OF THE PREFERRED EMBODIMENTS

In the description that follows, similar parts or structures used in the figures will be designated with like numerals, and where such parts and structures have been previously discussed with respect to an earlier figure, the description will not be repeated.

Figure 1:
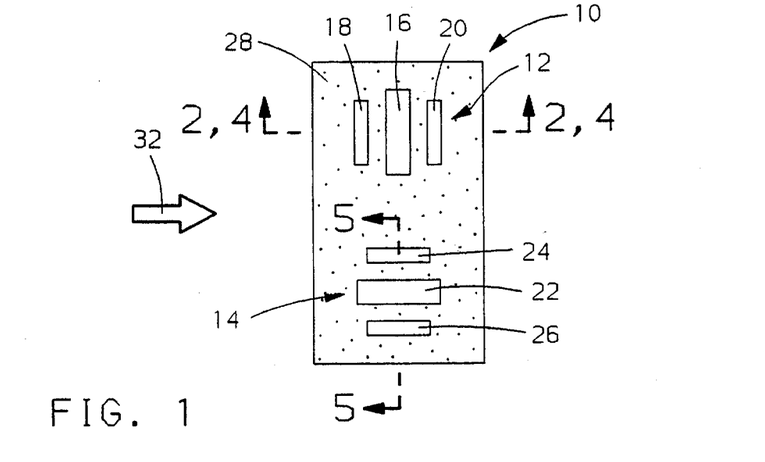
FIG. 1 schematically illustrates a plan view of a vapor composition and flow sensor according to the present invention.
Figure 2:
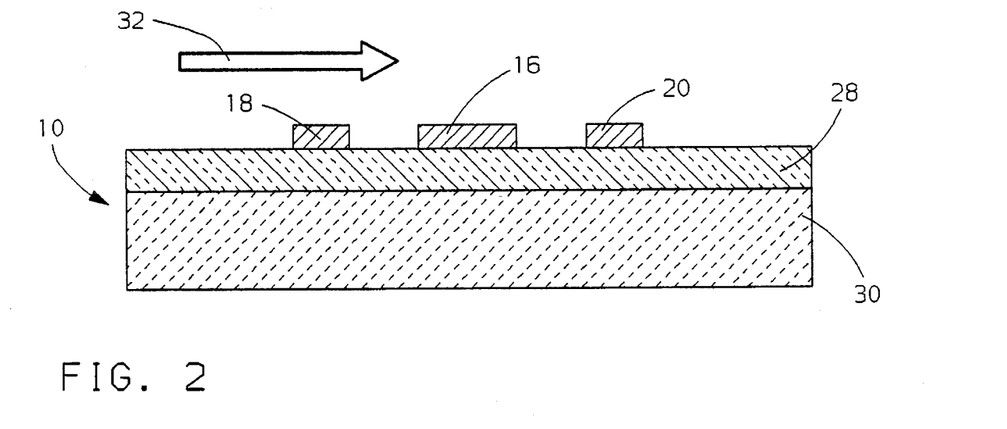
FIG. 2 schematically illustrates a side view of the vapor sensor of FIG. 1.

Referring to the drawings, and more particularly to FIGS. 1 and 2, reference numeral 10 generally designates a silicon-based integrated circuit chip vapor sensor in accordance with the present invention, positioned within a duct (not shown) through which a gaseous vapor is flowing. Arrow 32 illustrates the positive direction of air flow past the sensor 10. The sensor 10 comprises two orthogonal sensing patterns 12 and 14. A first sensing pattern 12 comprises a first heating element 16 in the form of a resistive strip extending across a portion of the sensor surface and positioned transversely to the vapor flow. The heating element 16 is also positioned equidistant between two thermoelectric temperature-detecting thermistor elements, one upstream 18 and one downstream 20 from the heating element 16. A second sensing pattern 14 similarly comprises a second heating element 22 positioned equidistant between two thermistor elements 24 and 26. However, the second sensing pattern 14 is positioned longitudinal to the vapor flow.

The heating elements 16 and 22, as well as their respective thermistor elements 18, 20, 24 and 26, are made from thin film platinum deposited on a thermally insulating polyimide layer 28 over a silicon base layer 30. Each heating element 16 and 22 is approximately 1 mm long and 50 μm wide. Each thermistor element 18, 20, 24 and 26 is approximately 0.8 mm long and 8 μm wide. The separation distance between the heating elements 16 and 22 and their respective thermistors 18, 20, 24 and 26 is approximately 50 μm.

Figure 3:
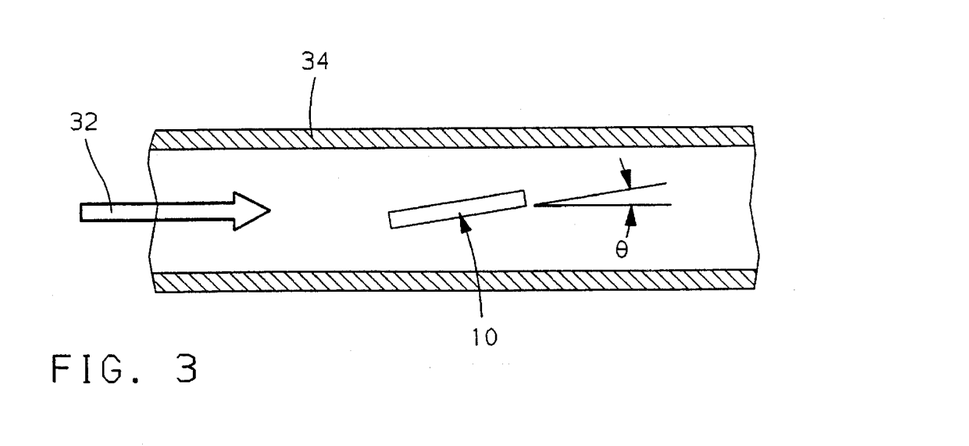
FIG. 3 schematically illustrates the positioning of the vapor sensor in a duct through which gaseous vapor is traveling.

As illustrated in FIG. 3, the vapor sensor 10 is positioned in the center of a duct 34 through which the gaseous vapor is flowing. The vapor sensor 10 is tilted by a predetermined number of degrees θ (e.g., 9°) with respect to the vapor flow direction for enhancing the sensitivity of the sensor 10.

Figure 4:
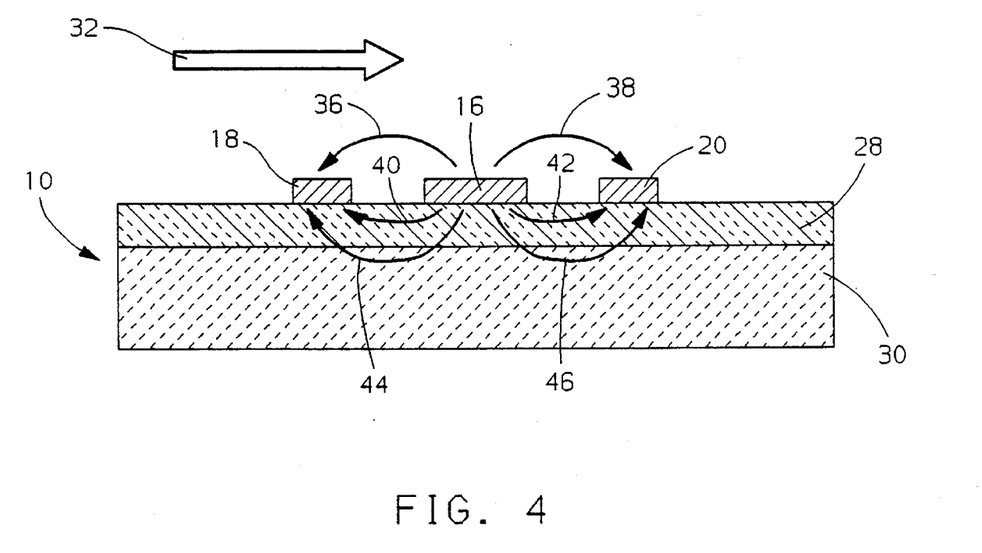
FIG. 4 illustrates the propagation of thermal waves within the first sensing pattern.

Referring to FIG. 4, when a sinusoidal voltage is applied to heating element 16 of the first sensing pattern 12, oscillatory thermal waves propagate outward from the heating element 16 to the upstream and downstream thermistors 18 and 20. The propagation of thermal waves are illustrated by arrows 36, 38, 40, 42, 44 and 46. The thermal waves represented by arrows 36 and 38 through the gas is substantially affected by the composition, direction and flow 32 of the gaseous vapor traveling through the duct 34. The remaining thermal waves illustrated by arrows 40, 42, 44 and 46 passing through the polyimide 28 and silicon 30 layers, are not substantially affected by either the gaseous vapor composition or flow.

Thermistors 18 and 20 are thermoelectric temperature-sensitive resistors, each having a resistance which varies directly with varying temperature. The temperature of each thermistor 18 and 20 is affected by the surrounding thermal waves 36–46. As thermal waves represented by arrows 36 and 38 propagate towards the upstream and downstream thermistors 18 and 20, respectively, the magnitude and phase of each thermal wave 36 and 38 is affected by the composition and flow of the gaseous vapor traveling past the sensing patterns 14 and 16. The upstream thermal wave 36 is affected in one way, while the downstream thermal wave 38 is affected in an opposite way. The difference between these two oscillatory waves is directly related to the composition and flow of the gaseous vapor.

The variations of the oscillating thermal waves 36 and 38 result in the resistances of the upstream and downstream thermistors 18 and 20 varying accordingly. As a result, by monitoring the resistances (i.e., temperature response) of the two thermistors 18 and 20, it is possible to obtain an indication of the composition and flow of the gaseous vapor. In particular, an output proportional to a difference between the downstream and upstream thermistor responses corresponds to the composition and flow of the gaseous vapor. For a sinusoidal power source $w(t)=W\cos(\omega t)$, this output may be approximated by the following equation:

$$|T_D - T_U| = [a/(8\pi(\omega)^{1/2})^{1/2}] * [Wu/K\alpha^{3/4}] * e[-a([\omega/2\alpha])^{1/2}]$$

where, $T_D = T(+a) =$ downstream thermistor temperature $T_U = T(-a) =$ upstream thermistor temperature a = distance between thermistor and heating element K = thermal conductivity of the gaseous vapor α = thermal diffusivity of the gaseous vapor u = speed of the gaseous vapor Note that the output signal of the first sensing pattern 12 is dependant upon both the speed of the gaseous vapor (u), as well as its composition through a dependence on its thermal properties (α and K).

Figure 5:
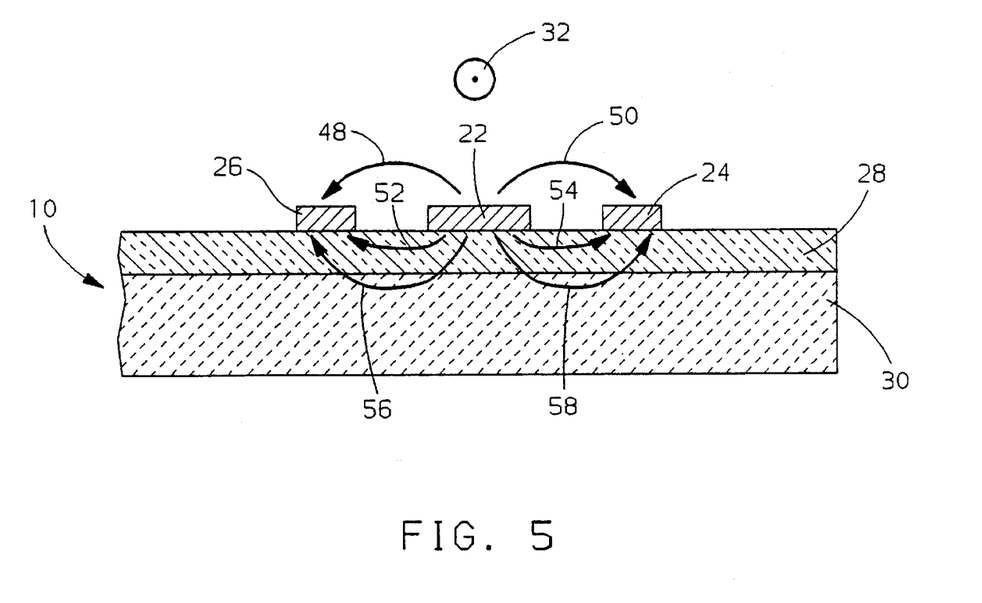
FIG. 5 illustrates the propagation of thermal waves within the second sensing pattern.

Referring to FIG. 5, when a sinusoidal voltage is similarly applied to heating element 22 of the second sensing pattern 14, oscillatory thermal waves propagate outward from the heating element 22 to the adjacent temperature-dependant thermistors 24 and 26. The propagation of thermal waves are illustrated by arrows 48, 50, 52, 54, 56 and 58. The thermal waves represented by arrows 48 and 50 passing through the gas are substantially affected by only the composition of the gaseous vapor traveling through the duct (note the flow 32 in this figure is coming directly out of the page). The remaining thermal waves illustrated by arrows 52, 54, 56 and 58 passing through the polyimide 28 and silicon 30 layers are not substantially affected by the gaseous vapor composition or flow.

As with thermistors 18 and 20, thermistors 24 and 26 are temperature-sensitive resistors, each having a resistance which varies directly with varying temperature. The temperature of each thermistor 24 and 26 is affected by thermal waves 48–58. As thermal waves represented by arrows 48 and 50 propagate towards the thermistors 24 and 26, the magnitude and phase of each thermal wave 48 and 50 is affected by primarily the composition of the gaseous vapor traveling past the sensing pattern 14. The effect of the vapor flow upon these thermal waves is negligible because of the longitudinal orientation of the thermistor elements 24 and 26 with respect to the flow direction, despite the presence of a small transverse flow component which may be caused by a slight misalignment of the sensing pattern 14 with respect to the flow direction 32.

The variations of the two thermal waves 36 and 38 result in the resistances of thermistors 24 and 26 varying accordingly. As a result, by monitoring the resistances (i.e., temperature response) of the two thermistors 24 and 26, it is possible to obtain an indication of the composition of the gaseous vapor. The output of the second sensing pattern 14 is proportional to a sum of the two thermistor signals, as approximated by the following equation:

$$T_R = W/(2\pi a \omega^{1/2})^{1/2} * \alpha^{1/4}/K * e[-a(\omega/2\alpha)^{1/2}] * \cos[\omega t - a9\omega/2\alpha)^{1/2} - \pi/8]$$

where, $T_R$=sum temperatures of the two thermistors
a=distance between a thermistor and heating element
K=thermal conductivity of the gaseous vapor
α=thermal diffusivity of the gaseous vapor Note that the output of the second sensing pattern 14 is not dependant upon flow (u), but rather only on the composition (α and K) of the gaseous vapor. Accordingly, the output of the second sensing pattern 14 is directly related to gas composition. Used in conjunction with the output of the first sensing pattern 12 which has an output voltage responsive to both composition and flow, the flow and composition dependant output of the first sensing pattern 12 can be adjusted to provide a flow-only voltage.

Figure 6:
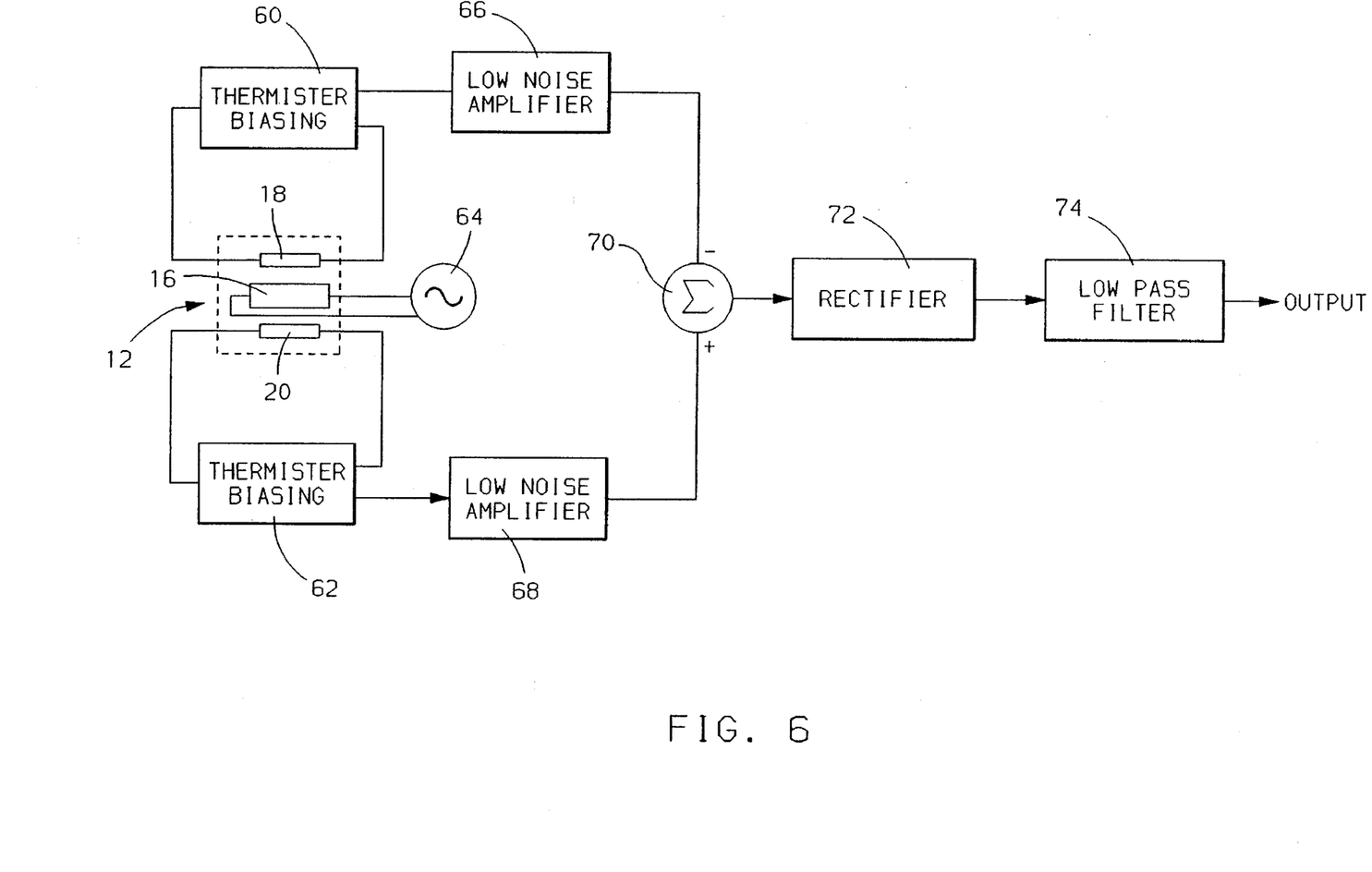
FIG. 6 schematically illustrates, in block diagram form, the electronic signal processing utilized for providing an output voltage from the first sensing pattern 12 corresponding to a combined gaseous vapor flow and composition dependant voltage.

FIG. 6 schematically illustrates, in block diagram form, the electronic signal processing utilized for providing an output voltage from the first sensing pattern 12 corresponding to a combined gaseous vapor flow and composition dependant voltage. Referring to FIG. 6, a power source 64 provides a sinusoidal output voltage to the heating element 16 of the first sensing pattern 12. This results in the generation of thermal waves sensed by the upstream 18 and downstream 20 thermistors. A first and second signal means 60 and 62 comprise thermistor biasing circuits. The outputs of the thermistor biasing circuits 60 and 62 carry signals indicative of the varying thermal wave signals sensed by thermistors 18 and 20. The output of circuits 60 and 62 are amplified by low-noise amplifiers 66 and 68 and a difference is found by subtracting means 70 comprising a summing circuit. Amplification via amplifiers 66 and 68 incorporates both magnitude and phase nulling capabilities to insure that both signals are identical at zero flow.

The resultant difference signal from summing circuit 70 is rectified by rectifier means 72 and filtered by low pass filter 74 to provide a usable flow- and composition-dependant output voltage signal. The output of the first sensing pattern 12 is not affected by the thickness of the polyimide 28 or silicon 30 layers because the thermal waves 40–46 are canceled when the upstream and downstream signals are differenced.

Figure 7:
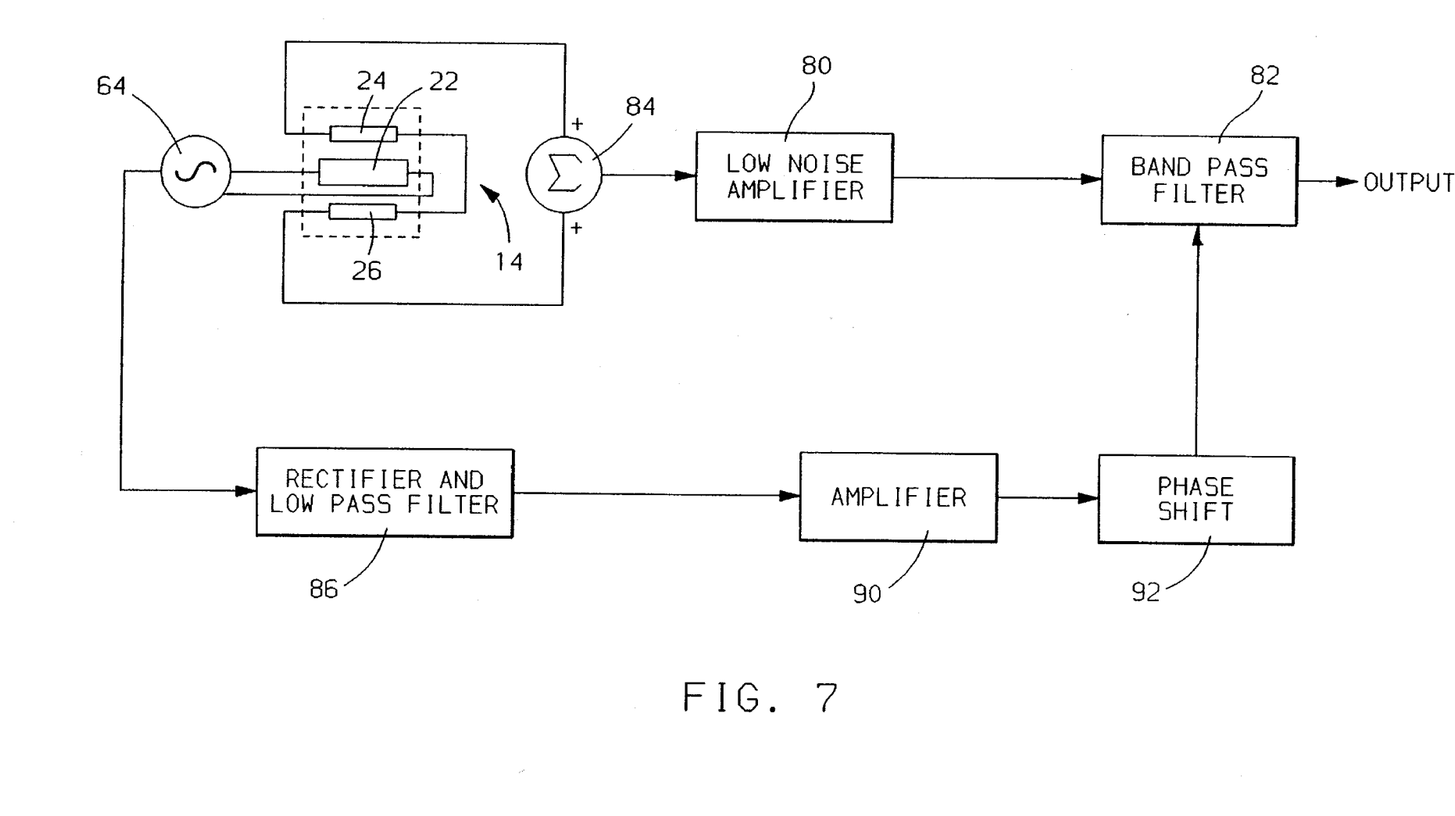
FIG. 7 schematically illustrates, in block diagram form, the electronic signal processing utilized for providing an output voltage from the second sensing pattern 12 corresponding to a gaseous vapor composition dependant voltage.
Figures 8, 9A:
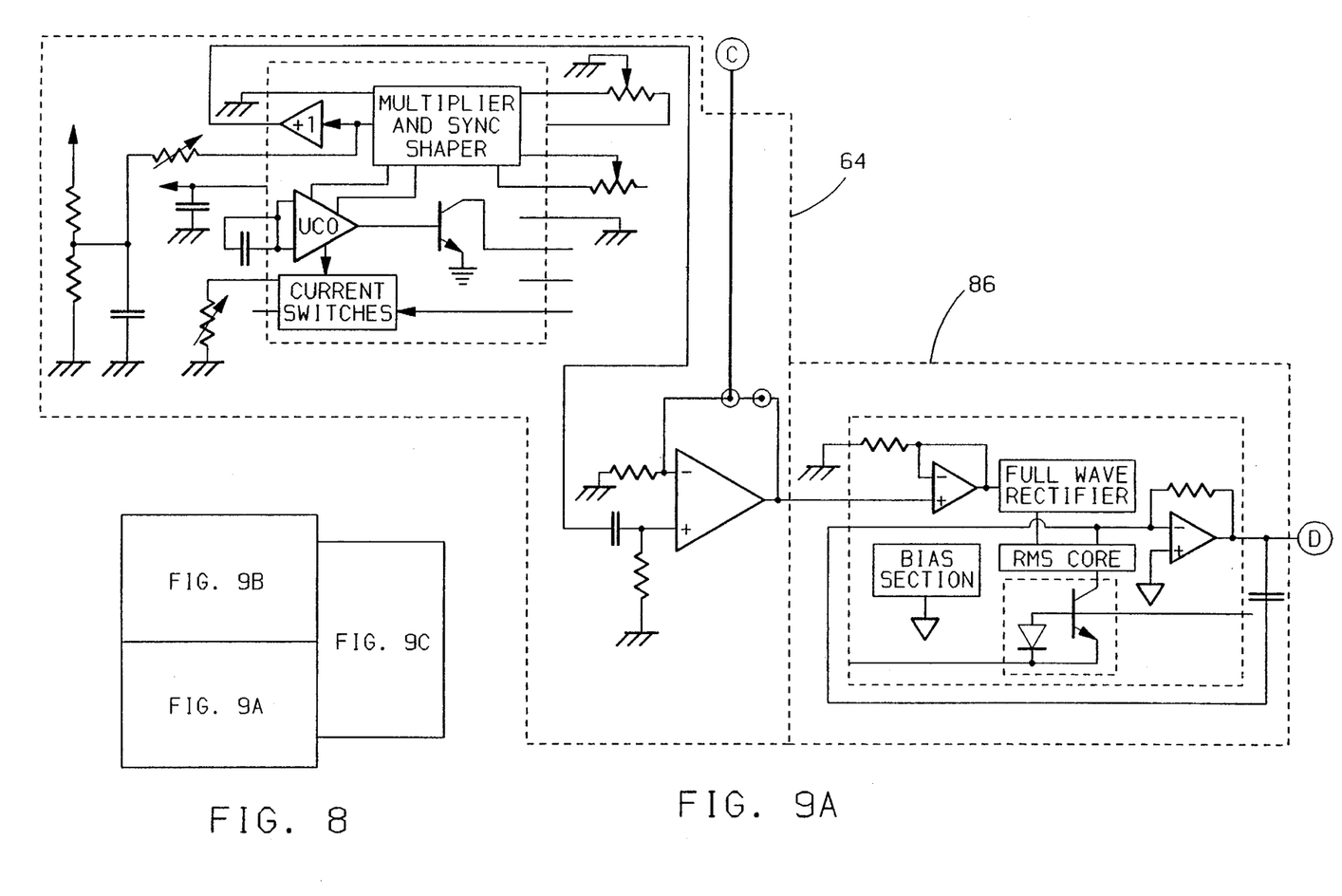
FIG. 8 illustrates a block diagram of the physical relationship of FIGS. 9A–C with one another.
FIGS. 9A–C illustrate a detailed electronic circuit diagram incorporating the functions identified in the schematic diagrams of FIGS. 6 and 7 for generating outputs responsive to the composition and flow of a gaseous vapor.
Figure 9B:
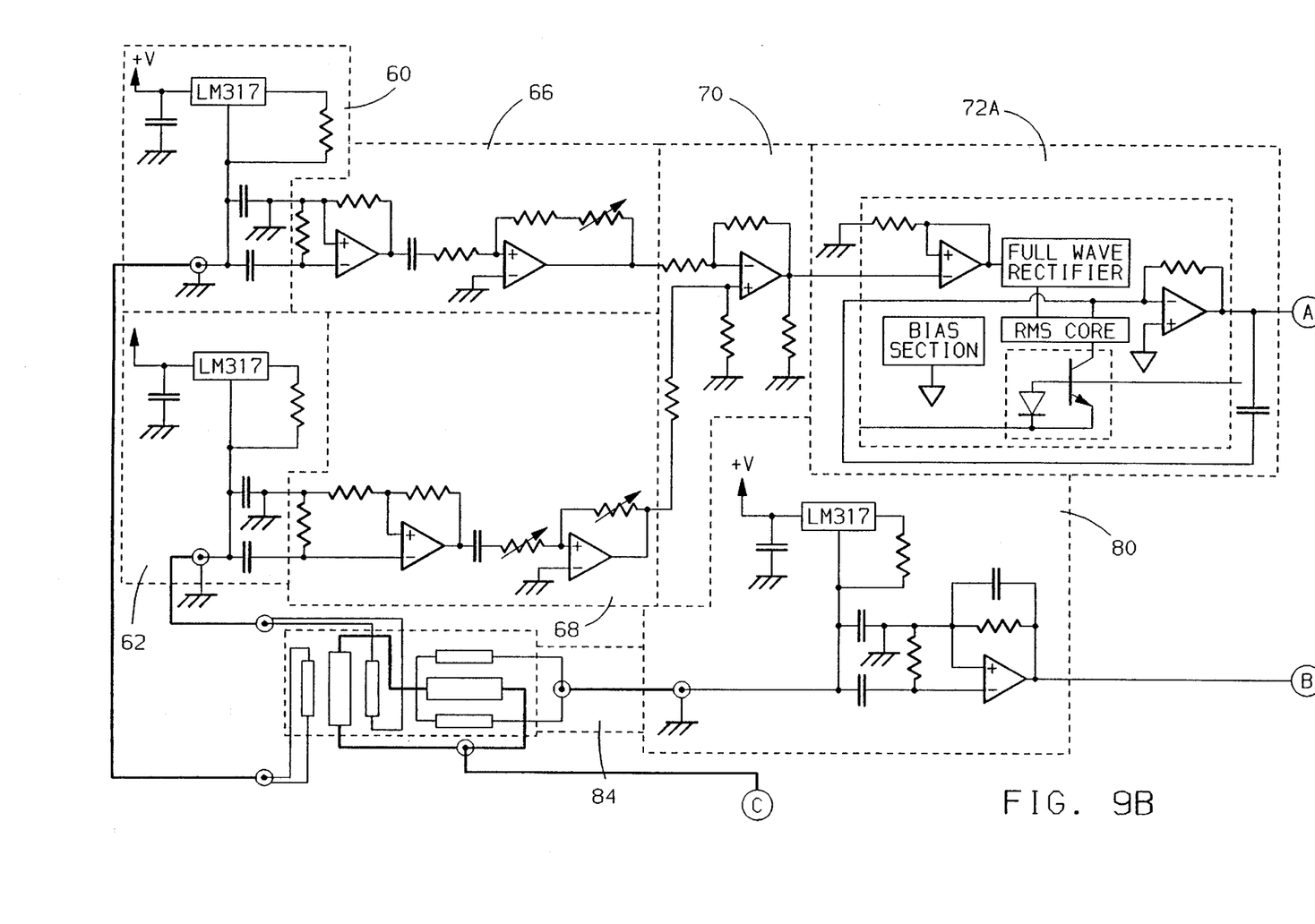
Figure 9C:
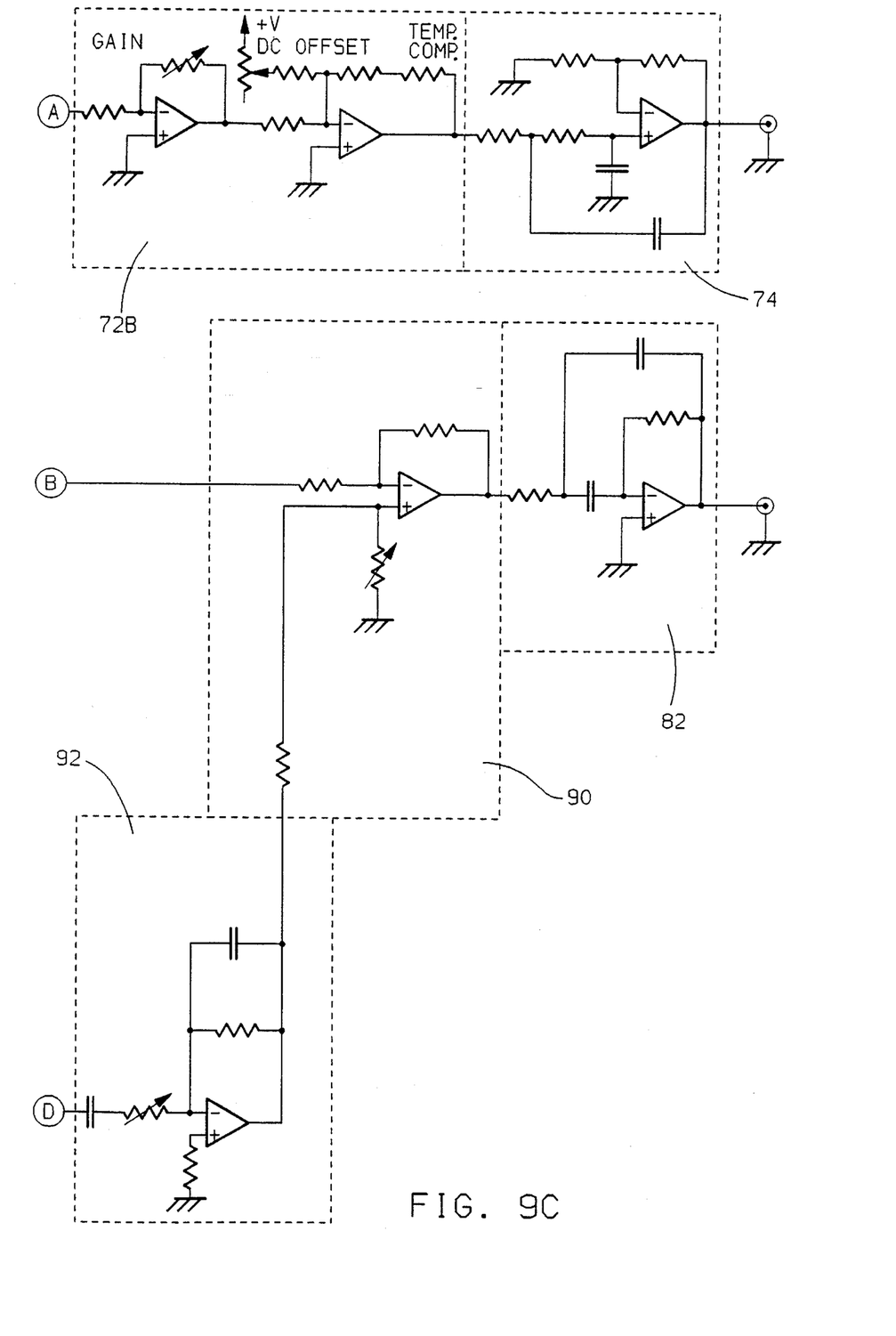

FIG. 7 schematically illustrates, in block diagram form, the electronic signal processing utilized for providing an output voltage from the second sensing pattern 12 corresponding to a gaseous vapor composition dependant voltage. Referring to FIG. 7, the power source 64 provides a sinusoidal output voltage to the heating element 22 of the second sensing pattern 14. This results in the generation of thermal waves 48–58 sensed by the two thermistors 24 and 26. The responses of the two thermistors 24 and 26 are summed by summing means 84, amplified by a low noise amplifier 80, and filtered by a band pass filter 82 with respect to a predetermined reference signal voltage.

Unlike the output of the first sensing pattern 12, the output of the second sensing pattern 14 is affected by the thickness of the polyimide 28 and silicon 30 layers because the thermal waves 52–58 passing through them are added rather than being differenced and thereby canceled. As a result, small lot-to-lot variations in the polyimide 28 and silicon 30 layer thicknesses may reduce the overall sensor repeatability.

FIG. 7 incorporates a technique for electronically canceling the effects of the thermal waves 52–58 passing through the polyimide 28 and silicon 30 layers. Electronic cancellation is achieved by rectifying and low pass filtering 86 the sinusoidal heater excitation signal provided from power source 64 so as to generate a signal at twice the heater frequency. This signal can then be amplified 90 and phase shifted 92 by appropriate amounts, whereupon the signal is input into the band pass filter 82 for modifying the predetermined reference signal voltage to cancel the affects of thermal waves 52–58.

FIGS. 8 and 9A–C illustrate a detailed electronic circuit diagram incorporating the functions identified in the schematic diagrams of FIGS. 6 and 7 for generating outputs responsive to the composition and flow of a gaseous vapor.

Figure 10:
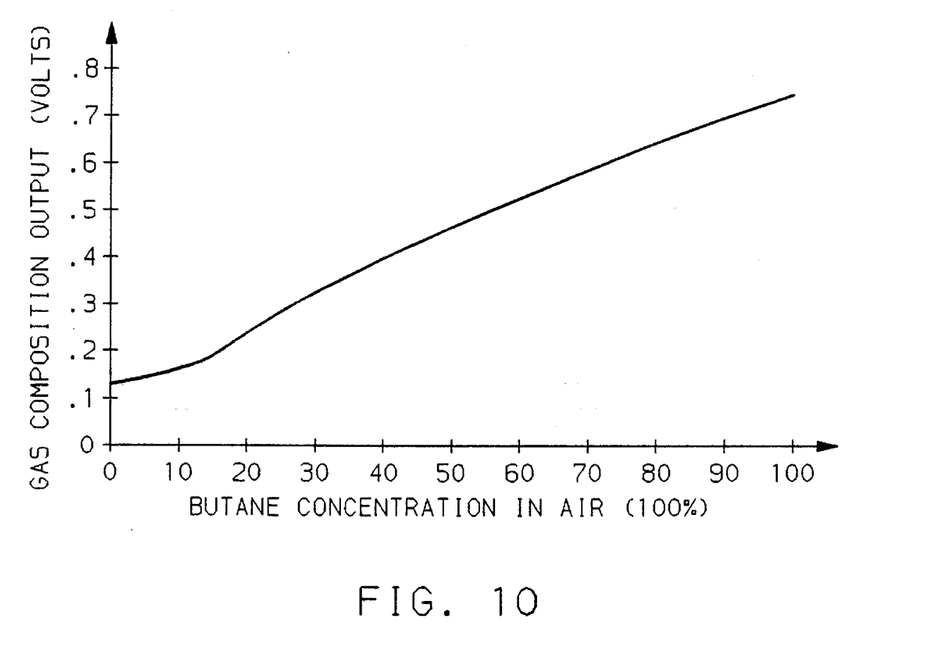
FIG. 10 illustrates a graph of the effects of gaseous vapor composition on the output voltage of the second sensing pattern.
Figure 11:
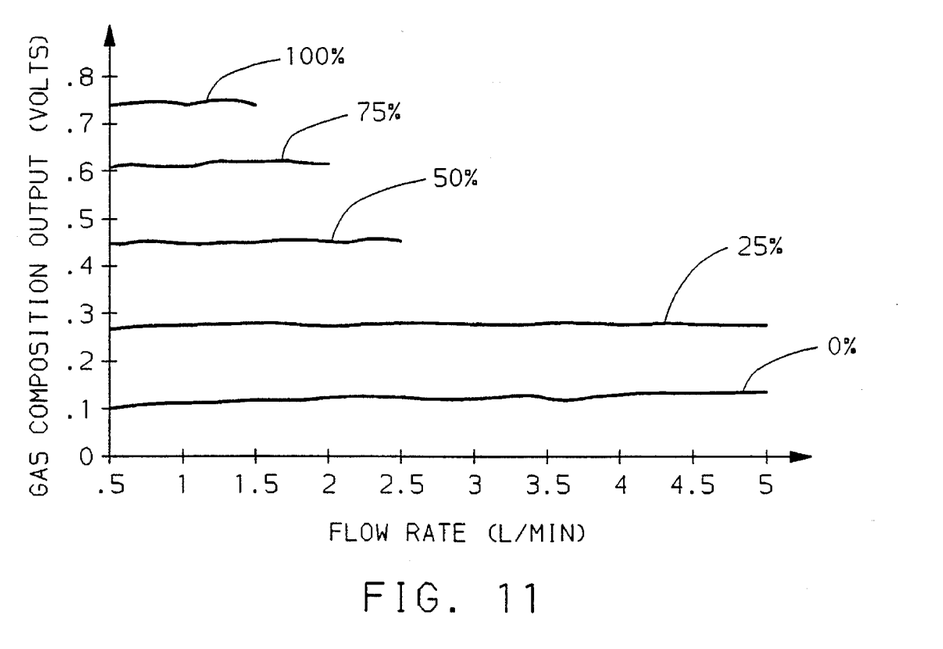
FIG. 11 illustrates a graph of the effects of flow rate on the output voltage of the second sensing pattern.

FIG. 10 illustrates the affects of the gaseous vapor composition on the output voltage of the second sensing pattern 14 for the case of air-butane mixtures ranging from 0 to 100% butane concentration. Note that the output voltage signal varies generally linearly with varying concentration. However, referring to FIG. 11, note that the output voltage of the second sensing pattern 14 is generally not affected by the flow rate.

Figure 12:
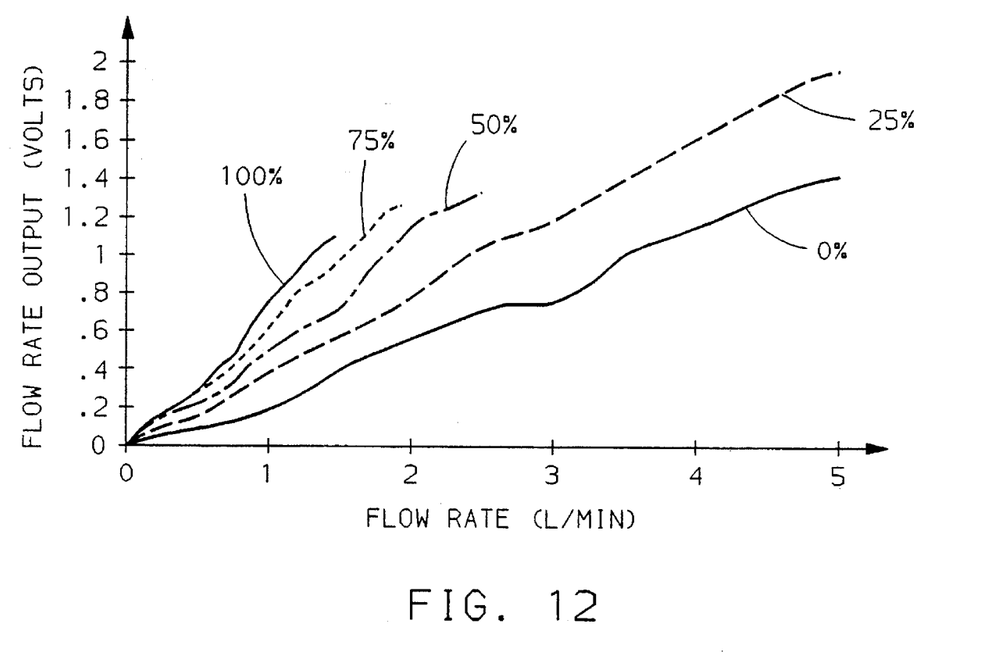
FIG. 12 illustrates a graph of the affects of gaseous vapor composition on the output voltage of the first sensing pattern.

FIG. 12 illustrates the output voltage signal of the first sensing pattern 12 as a function of the gaseous vapor flow rate, for different butane % concentrations in air. Note that the output signals increase monotonically with flow for varying butane concentrations. Note also that when the flow rate is fixed, the output increases as the butane concentration increases. It is therefore possible to identify the correct flow rate from the flow- and composition-dependant output voltage signal of the first sensing pattern 12 by using the composition-dependant output voltage signal of the second sensing pattern 14 to identify the correct calibration curve of FIG. 12. For example, the 25% butane calibration curve is used to determine flow rate if the gaseous vapor composition output is ~0.28 volts. A flow of 2.5 liters/minute would then be inferred if the simultaneous flow output is ~1 volt.

While the present invention has been described in reference to the illustrated embodiments, it will be recognized that various modifications will occur to those skilled in the art. In this regard, it will be understood that apparatuses incorporating such modifications may fall within the scope of this invention, which is defined by the appended claims.

The embodiments of this invention in which an exclusive property or privilege is claimed are defined as follows:

1. An apparatus for providing gaseous vapor output signals indicative of the composition and flow of the gaseous vapor traveling through a duct, the apparatus comprising:

a first sensing pattern including a first heater positioned equidistant between an upstream detector and a downstream detector, the first heater as well as the upstream and downstream detectors positioned transversely within the duct and responsive to temperature;

a second sensing pattern including a second heater positioned equidistant between a first detector and a second detector, the second heater as well as the first and second detectors positioned longitudinally within the duct and responsive to temperature; and means for exciting the first and second heaters to generate sinusoidal thermal waves which propagate through the gaseous vapor to the upstream and downstream detectors and the first and second detectors, respectively, resulting in temperature variations and corresponding responses by the upstream, downstream, first and second detectors, wherein the responses of the upstream and downstream detectors are dependant upon the composition and flow of the gaseous vapor and the responses of the first and second detectors are dependant upon only the composition of the gaseous vapor.

2. The gaseous vapor composition and flow sensing apparatus according to claim 1, further comprising:

first signal means for providing a first signal responsive to the propagating thermal waves sensed by the upstream detector;

second signal means for providing a second signal responsive to the propagating thermal waves sensed by the downstream detector;

third signal means for providing a third signal responsive to the propagating thermal waves sensed by the first detector;

fourth signal means for providing a fourth signal responsive to the propagating thermal waves sensed by the second detector;

means for subtracting the first and second signals to obtain a difference signal;

means for adding the third and fourth signals to obtain a cumulative signal;

means for providing a gaseous vapor composition output signal responsive to the cumulative signal and indicative of a measure of the composition of the gaseous vapor; and means for providing a first gaseous vapor flow output signal responsive to the difference signal and indicative of both the composition and flow of the gaseous vapor.

3. The gaseous vapor composition and flow sensing apparatus according to claim 2, further comprising:

means for providing a second gaseous vapor flow output signal responsive to both the difference and cumulative signals, and indicative of the flow of the gaseous vapor.

4. The gaseous vapor composition and flow sensing apparatus according to claim 1, wherein the first and second heaters, as well as the upstream, downstream, first and second detectors are formed of thin film platinum deposited on a thermally insulating polyimide layer over a silicon layer.

5. The gaseous vapor composition and flow sensing apparatus according to claim 1, wherein the upstream, downstream, first and second detectors are one of thermistors and thermocouples.

6. The gaseous vapor composition and flow sensing apparatus according to claim 1, wherein the sensing apparatus is positioned at a predetermined angle with respect to the gaseous vapor flow.

* * * * *